United States Patent [19]
Tokuyama

[11] Patent Number: 6,030,823
[45] Date of Patent: Feb. 29, 2000

[54] D-AMINOACYLASE

[75] Inventor: Shinji Tokuyama, Shizuoka, Japan

[73] Assignee: Daicel Chemical Industries, Ltd., Osaka, Japan

[21] Appl. No.: 09/268,941

[22] Filed: Mar. 16, 1999

[30] Foreign Application Priority Data

Mar. 17, 1998 [JP] Japan .................................. 10-089246
Feb. 15, 1999 [JP] Japan .................................. 11-035620

[51] Int. Cl.⁷ .............................. C12N 9/78; C12N 9/14; C12N 9/10
[52] U.S. Cl. ......................... 435/227; 435/183; 435/193; 435/195; 435/228
[58] Field of Search ..................................... 435/227, 228, 435/193, 183, 195

[56] References Cited

PUBLICATIONS

Wayayama et al. Biosci. Biotech Chem. 59. p. 2115, 1995.

Sugie et al. Agric Biol Chem. 44. p. 1089, 1980.

Tsai et al. Microb techn. 14 p. 382, 1992.

*Primary Examiner*—Leon B. Lankford, Jr.
*Attorney, Agent, or Firm*—Fish & Richardson P.C.

[57] ABSTRACT

A novel D-aminoacylase was derived from a microorganism belonging to the genus Sebekia. This enzyme is useful for producing D-amino acids from N-acetyl-DL-amino acids on an industrial scale.

7 Claims, 6 Drawing Sheets

D-AMINOACYLASE

FIELD OF THE INVENTION

The present invention relates to a novel D-aminoacylase and a method of producing D-amino acids using said D-aminoacylase.

BACKGROUND OF THE INVENTION

Enzymes have excellent catalytic functions with substrate specificity, reaction specificity, and stereospecificity.

Stereospecificity of enzymes, with some exceptions, are nearly absolute.

Recent precise research has increased the importance of optically active substances for use in drugs, pesticides, feeds, and perfumes. Optical isomers sometimes have quite different biological activities. D(R)-form thalidomide has no teratogenic activity, but its L(S)-form shows strong teratogenicity. The practical use of thalidomide racemate caused the drug injury incidents. If one enantiomer shows an effective biological activity, the other enantiomer may sometimes have no activity, rather, it may competitively inhibit the activity of the effective enantiomer. In some cases, the activity of the racemate is reduced to half or less of the activity of the effective enantiomer. Accordingly, it is industrially important to obtain (synthesize or optically resolve) optically pure enantiomers. For this purpose, techniques for effective resolution of synthetic racemate have been widely used. Enzymatic optical resolution has drawn attention because it does not produce by-products and a bulk of liquid waste.

Generally, L-amino acids are widely and largely utilized in seasonings, food and feed additives, and infusions and are thus very highly demanded. L-Amino acids have been produced mainly by direct fermentation using microorganisms. Optical resolution is also a known method for producing L-amino acids by hydrolyzing N-acyl-DL-amino acids using L-aminoacylases. It has been utilized toindustrially produce L-amino acids that are difficult to produce by fermentation. L-aminoacylases are widely found in animals, plants, and microorganisms. They have been purified from various organisms, and their properties have been clarified.

N-terminal amino acids of many proteins are considered to be N-acetylated in vivo. L-Aminoacylases presumably regenerate N-acetyl-amino acids produced by decomposition of proteins to amino acids. Among L-aminoacylases, acylase, which acts on N-acyl-L-glutamic acid, is reportedly involved in arginine biosynthesis (Fruth, H., Leisinger, T.: J. Gen. Microb. 125, ppl (1981)).

In contrast, D-amino acids have not been a subject of interest for a long time because they are nonprotein amino acids. D-amino acids were known to occur in small cyclic peptides, peptidoglycan of bacterial cell walls, and peptide antibiotics. However, D-amino acids have been demonstrated to be constituents of neuro peptides and to exist as binding forms in tooth enamel, the lens, and cerebral proteins, resulting in investigation of physiological significance and enzymatic synthesis of D-amino acids.

At present, DL-amino acids have been optically resolved by physicochemical, chemical, and enzymatic methods. The enzymatic methods are the most convenient and industrially applicable for, for example, continuously producing L-methionine from N-acetyl-DL-methionine using a bioreactor of immobilized L-aminoacylase. D-amino acids may also be produced using hydantoinase. The method consists of two-step enzymatic reactions. The first reaction uses D-specific hydantoinase to convert D,L-5-substituted-hydantoin, which is synthesized at low cost from aldehyde analogues, to a D-carbamyl derivative. The second reaction uses D-amino acid carbamylase. Another method comprises hydrolyzing N-acetyl-DL-amino acids with D-aminoacylase to produce D-amino acids (Sugie, M. and Suzuki, H.: Argric. Biol. Chem. 44, pp1089 (1980), Tsai, Y. C., Lin, C. S., Tseng, T. H., Lee, H. and Wang, Y. J.: J. Enzyme Microb. Technol. 14, pp384 (1992)). D-aminoacylase is important in D-amino acid production, but its physiological significance and structural functions remain to be clarified.

D-aminoacylase was first reported to be found in Pseudomonas sp. KT83 isolated from soil by Kameda et. al in 1952 (Kameda, Y., Toyoura, H., Kimura, Y. and Yasuda, Y.: Nature 170, pp888 (1952)). This enzyme hydrolyzed N-benzoyl derivatives of D-phenylalanine, D-tyrosine, and D-alanine. Thereafter, D-aminoacylases were derived from microorganisms belonging to the genus Pseudomonas (Kubo, K., Ishikura, T., and Fukagawa, Y.: J. Antibiot. 43, pp550 (1980), Kubo, K., Ishikura, T. and Fukagawa, Y.: J. Antibiot. 43, pp556 (1980), Kameda, Y., Hase, T., Kanatomo, S. and Kita, Y.: Chem. Pharm. Bull. 26, pp2698 (1978),Kubo, K., Ishikura, T. and Fukagawa, Y.: J. Antibiot. 43, pp543 (1980)), the genus Streptomyces (Sugie, M. and Suzuki, H.: Argric. Biol. Chem. 42, pp107 (1978), Sugie, M. and Suzuki, H.: Argric. Biol. Chem. 44, pp1089 (1980)), and the genus Alcaligenes (Tsai, Y. C., Tseng, C. P., Hsiao, K. M. and Chen, L. Y.: Appl. Environ. Microbiol. 54, pp984 (1988), Yang, Y. B., Hsiao, K. M., Li, H., Yano, Y., Tsugita, A. and Tsai, Y. C.: Biosci. Biotech. Biochem. 56, pp1392 (1992), Yang, Y. B., Lin, C. S., Tseng, C. P., Wang, Y. J. and Tsai, Y. C.: Appl. Environ. Microbiol. 57, pp2767 (1991), Tsai, Y. C., Lin, C. S., Tseng, T. H., Lee, H. and Wang: Microb. Technol. 14, pp384 (1992), Moriguchi, M. and Ideta, K.: Appl. Environ. Microbiol. 54, pp2767 (1988), Sakai, K., Imamura, K., Sonoda, Y., Kido, H. and Moriguchi, M.: FEBS, 289, pp44 (1991), Sakai, K., Obata, T., Ideta, K. and Moriguchi, M.: J. Ferment. Bioeng. 71, pp79 (1991), Sakai, K., Oshima, K. and Moriguchi, M.: Appl. Environ. Microbiol. 57, pp2540 (1991), Moriguchi, M., Sakai, K., Katsuno, Y., Maki, T. and Wakayama, M.: Biosci. Biotech. Biochem., 57, pp1145 (1993), Kayama, M., Ashika, T., Miyamoto, Y., Yoshikawa, T., Sonoda, Y., Sakai, K. and Moriguchi, M.: J. Biochem. 118, pp204 (1995)), Moriguchi, M., Sakai, K., Miyamoto, Y. and Wakayama, M.: Biosci. Biotech. Biochem., 57, pp1149 (1993)).

Tsai et al. and Moriguchi et al. also clarified the characteristics of D-aminoacylase derived from microorganisms belonging to the genera Alcaligenes and Pseudomonas and the amino acid and nucleotide sequences of the enzymes. Moriguchi et al. found that microorganisms belonging to the genera Alcaligenes and Pseudomonas produced three species of D-aminoacylase by using different inducers (Wakayama, M., Katsumo, Y., Hayashi, S., Miyamoto, Y., Sakai, K. and Moriguchi, M.: Biosci. Biotech. Biochem. 59, pp2115 (1995).

Furthermore, Moriguchi et al. determined the nucleotide sequences of these D-aminoacylases derived from a microorganism belonging to the genus Alcaligenes and compared it with L-aminoacylases derived from *Bacillus stereothermophilus*, human, and pig. The result demonstrated that these D-aminoacylases have a low homology with L-aminoacylases (Wakayama, M., Katsuno, Y., Hayashi, S., Miyamoto, Y., Sakai, K. and Moriguchi, M.: Biosci. Biotech.

Biochem., 59, pp2115 (1995)).

Sugie et al. reported D-aminoacylase of a microorganism belonging to the genus Streptomyces of actinomycetes (Sugie, M. and Suzuki, H.: Argric. Biol. Chem. 42, pp107 (1978), Sugie, M. and Suzuki, H.: Argric. Biol. Chem. 44, pp1089 (1980)). However, the enzyme has not been purified yet, and the characteristics remain unknown.

SUMMARY OF THE INVENTION

An objective of the present invention is to provide a new D-aminoacylase derived from a microorganism. Another objective of the present invention is to provide a method of producing D-amino acids using said D-aminoacylase.

As a result of the investigation to achieve the above objectives, the present inventors succeeded in purifying D-aminoacylase having novel properties from a microorganism belonging to the genus Sebekia by combining various purification methods. The present inventors also found that purified D-aminoacylase is useful for industrially producing D-amino acids.

The present invention relates to a D-aminoacylase having novel properties derived from a microorganism. More specifically, the present invention relates to, (1) a D-aminoacylase having the following physicochemical properties:
  (a) Action: acting on N-acetyl-D-amino acid to produce D-amino acid;
  (b) Molecular weight: about 55,000 daltons determined by SDS-polyacrylamide gel electrophoresis and about 36,000 to about 37,000 daltons determined by gel filtration;
  (c) Substrate specificity: acting on N-acetyl-D-methionine, N-acetyl-D-valine, N-acetyl-D-tryptophan, N-acetyl-D-asparagine, N-acetyl-D-phenylalanine, N-acetyl-D-alanine, and N-acetyl-D-leucine, but not on N-acetyl-L-methionine, N-acetyl-L-leucine, and N-acetyl-L-valine;
  (d) Thermostability: stable at 40° C. and inactivated at 50° C. or above when heated at pH 7.5 for 30 minutes;
  (e) Optimum temperature: optimally active at about 45° C. when reacted at pH 7.5;
  (f) Optimum pH: optimally active at a pH of about 7.5 to about 8.5 when reacted at 30° C. for 30 minutes; and
  (g) Effects of metal ions: requiring no metal ion, but inhibited by 1 mM of $Cu^{2+}$, $Hg^{2+}$, $Ni^{2+}$, $Fe^{2+}$, $CO^{2+}$, and $Zn^{2+}$;

(2) the D-aminoacylase of (1), which is derived from a microorganism belonging to the genus Sebekia;

(3) a method of producing the D-aminoacylase of (1), which comprises culturing a microorganism belonging to the genus Sebekia and recovering an enzyme having the following properties:
  (a) Action: acting on N-acetyl-D-amino acid to produce D-amino acid;
  (b) Molecular weight: about 55,000 daltons determined by SDS-polyacrylamide gel electrophoresis and about 36,000 to about 37,000 daltons determined by gel filtration;
  (c) Substrate specificity: acting on N-acetyl-D-methionine, N-acetyl-D-valine, N-acetyl-D-tryptophan, N-acetyl-D-asparagine, N-acetyl-D-phenylalanine, N-acetyl-D-alanine, and N-acetyl-D-leucine, but not on N-acetyl-L-methionine, N-acetyl-L-leucine, and N-acetyl-L-valine;
  (d) Thermostability: stable at 40° C. and inactivated at 50° C. or above when heated at pH 7.5 for 30 minutes;
  (e) Optimum temperature: optimally active at about 45° C. when reacted at pH 7.5;
  (f) Optimum pH: optimally active at a pH of about 7.5 to about 8.5 when reacted at 30° C. for 30 minutes; and
  (g) Effects of metal ions: requiring no metal ion, but inhibited by 1 mM of $Cu^{2+}$, $Hg^{2+}$, $Ni^{2+}$, $Fe^{2+}$, $Co^{2+}$, and $Zn^{2+}$;

(4) a method of producing D-amino acid which comprises reacting N-acetyl-DL-amino acid with the D-aminoacylase of (1); and (5) the method of (4), wherein said N-acetyl-DL-amino acid is selected from the group consisting of N-acetyl-DL-methionine, N-acetyl-DL-valine, N-acetyl-DL-tryptophan, N-acetyl-DL-asparagine, N-acetyl-DL-phenylalanine, N-acethyl-DL-alanine, and N-acethyl-DL-leucine.

DETAILED DESCRIPTION OF THE INVENTION

The present invention relates to a novel D-aminoacylase derived from a microorganism having the following physicochemical properties:

(a) Action: acting on N-acetyl-D-amino acid to produce D-amino acid;
(b) Molecular weight: about 55,000 daltons determined by SDS-polyacrylamide gel electrophoresis and about 36,000 to about 37,000 daltons determined by gel filtration;
(c) Substrate specificity: acting on N-acetyl-D-methionine, N-acetyl-D-valine, N-acetyl-D-tryptophan, N-acetyl-D-asparagine, N-acetyl-D-phenylalanine, N-acetyl-D-alanine and N-acetyl-D-leucine, but not on N-acetyl-L-methionine, N-acetyl-L-leucine, and N-acetyl-L-valine;
(d) Thermostability: stable at 40° C. and inactivated at 50° C. or above when heated at pH 7.5 for 30 minutes;
(e) Optimum temperature: optimally active at about 45° C. when reacted at pH 7.5;
(f) Optimum pH: optimally active at a pH of about 7.5 to about 8.5 when reacted at 30° C. for 30 minutes; and
(g) Effects of metal ions: requiring no metal ion, but inhibited by 1 mM of $Cu^{2+}$, $Hg^{2+}$, $Ni^{2+}$, $Fe^{2+}$, $Co^{2+}$, and $Zn^{2+}$.

The D-aminoacylase of the present invention may be derived from any organisms as long as it contains the physicochemical properties as described above. It is preferably derived from a microorganism belonging to the genus Sebekia, specifically *Sebekia benihana*, more specifically *Sebekia benihana* IFO14309 (as listed in List of Cultures, Institute for Fermentation, Osaka (1996) and available from the Institute (17-85, Juso-honmachi 2-chome, Yodogawa-ku, Osaka 532 Japan)). The microorganism to be used may be wild strains, variants, or recombinant strains produced by genetic techniques such as cell fusion or gene manipulation.

The D-aminoacylase of the present invention can be prepared using the method for assaying the enzymatic activity and purifying said enzyme as described in the following Examples. Specifically, the enzyme can be prepared by culturing the above-described microorganism under the conditions that it produces the desired enzyme and recovering the enzyme having the above-described physicochemical properties from the culture.

The culture medium used for culturing the microorganism to be used in the present invention is not particularly limited as long as the microorganism can proliferate therein. Any carbon source, which is usable by the above-described microorganism, can be used. Examples thereof include sugars such as glucose, fructose, sucrose, and dextrin, alcohol such as sorbitol and glycerol, organic acids such as fumaric acid, citric acid, acetic acid, and propionic acid and the salts thereof, hydrocarbons such as paraffin, and mixtures of these materials. Examples of nitrogen sources include ammonium salts of inorganic acids such as ammonium chloride, ammonium sulfate, and ammonium phosphate, ammonium salts of organic acids such as ammonium fumarate, and ammonium citrate, meat extract, yeast extract, corn steep liquor, hydrolysate of casein, inorganic or organic nitrogen-containing compounds such as urea, and mixtures of these materials. In addition, nutrients that are used for ordinary culture such as organic salts, trace mineral salts, and vitamins may be mixed as needed.

The microorganism is cultured in the presence of an inducer for the enzyme production. Examples of the inducer include D-valine, D-tryptophan, D-phenylalanine, or the like.

The microorganism can be cultured under any condition that it grows. Specifically, the microorganism can be cultured in the culture medium at the pH of usually 2 to 12, preferably 4 to 10, and at the temperature of usually 5 to 60° C., preferably 20 to 40° C., for the culturing period of usually several hours to ten days until activity of the enzyme produced becomes maximum.

The enzyme produced can be recovered by collecting the cultured microbial cells from the culture medium by, for example, centrifugation, disrupting the cells by, for example, ultrasonication, lysis with lysozyme, or the like. The thus-obtained cell-free extract is subjected to various purification methods usually used in the art, including ion exchange chromatography, gel filtration, fractionation with ammonium sulfate, and the like to give the purified enzyme.

The D-aminoacylase of the present invention acts on various N-acetyl-DL-amino acids to produce corresponding D-amino acids and thus enables producing D-amino acids industrially. For example, the D-aminoacylase is reacted with N-acetyl-DL-amino acids to produce D-amino acids. Suitable examples of the N-acetyl-DL-amino acids include N-acetyl-DL-methionine, N-acetyl-DL-valine, N-acetyl-DL-tryptophan, N-acetyl-DL-asparagine, N-acetyl-DL-phenylalanine, N-acetyl-DL-alanine, and N-acetyl-DL-leucine.

In the production of D-amino acids of the present invention, it is possible to use not only the purified enzyme but also the crude enzyme as obtained above, the cultured microorganism, and the treated product of the microorganism. The microorganism can be used in a state of the culture medium, cells separated from the culture medium by centrifugation or the like, or cells resuspended in buffer, water, or the like after they are separated by centrifugation and washed. The microbial cells can be used in a state as they are recovered, as their disrupts, as treated with acetone or toluene, or as lyophilizate. The microbial cells can also be used by being immobilized on carageenan gel, alginate gel, polyacrylamide gel, cellulose, agar, or the like supporting material, using a known method. The enzyme can also be used in the immobilized form. It can be immobilized on the supporting material as described above by a known method.

The concentration of N-acetyl-DL-amino acid to be used as a substrate is not particularly limited. It usually ranges from about 0.1 to about 30 w/v %. Though using the D-aminoacylase in a large quantity often accelerates the reaction rate, it is usually used in an amount of about 1 to about 1000 U/ml. One unit of the enzyme is defined as the amount of the enzyme to produce 1 μmol of D-methionine at 30° C. in 1 min when the enzyme is reacted with N-acetyl-DL-methionine as the substrate. The reaction can be conducted at 5 to 50° C., preferably 30 to 40° C., and at pH 4 to 10, preferably 7 to 9. The reaction time is determined based on quantities of the D-aminoacylase and a substrate and generally ranges from 10 to 100 hours, preferably 10 to 50 hours. The reaction medium to be used includes water, a buffer, an aqueous organic solvent such as alcohols, and a double phase solution of water and a water-immiscible organic solvent such as toluene.

The D-amino acids produced can be recovered from the reaction mixture by a known method such as direct crystallization by concentration or isoelectric precipitation, ion exchange resin treatment, membrane filtration, or the like.

For example, D-tryptophan produced using N-acetyl-DL-tryptophan as a substrate can be purified as follows. After the enzymatic reaction, the reaction mixture is contacted with strongly acidic cation exchange resin to adsorb D-tryptophan. The resin was washed with water and eluted with 0.5 N aqueous ammonia. After the eluate was concentrated, the thus-obtained crude crystalline powder of D-tryptophan is dissolved in a small amount of 50% hot ethanol, decolorized with activated charcoal, and cooled to obtain purified crystals of D-tryptophan.

In the method of the present invention, D-valine can be purified as follows. After the enzymatic reaction, the microbial cells are removed by centrifugation or the like, and the resulting supernatant is adjusted to pH 1 by adding 6N hydrochloric acid. The precipitated N-acetyl-L-valine is removed by centrifugation. The supernatant is treated with activated charcoal, adjusted to pH 7.0, then added to an $H^+$-type strongly acidic cation exchanger (Amberlite IR-120B). Elution is performed with 5% aqueous ammonia, and the resulting eluate is dried at 80° C. under reduced pressure, thereby producing D-valine.

As described above, the present invention provides a D-aminoacylase derived from a microorganism belonging to the genus Sebekia and a method of producing D-amino acids using the same. The enzyme of the present invention can be reacted with N-acetyl-DL-amino acids such as N-acetyl-DL-methionine, N-acetyl-DL-valine, N-acetyl-DL-tryptophan, N-acetyl-DL-aspargine, N-acetyl-DL-phenylalanine, N-acetyl-DL-alanine, or N-acetyl-DL-leucine to produce the corresponding D-amino acids simply and efficiently.

The following examples illustrate the present invention in more detail, but are not to be construed to limit the scope of the present invention.

EXAMPLE 1

Purification of D-aminoacylase Derived From *Sebekia benihana* IFO14309

1. Induction of D-aminoacylase

Three methods of culturing *Sebekia benihana* IFO14309 were investigated to induce D-aminoacylase.

First, *Sebekia benihana* IFO14309 was cultured with shaking for 74 hours in test tubes, each containing 8.0 ml of PY liquid medium (0.2% glycerol, 2.0% yeast extract, 2.0% polypeptone, pH 7.3) supplemented with 0.10% DL-leucine, 0.10% N-acetyl-DL-leucine, 0.10% DL-methionine, 0.10% N-acetyl-DL-methionine, DL-valine, or 0.10% N-acetyl-DL-valine as inducers (experiment 1).

Second, a seed culture was prepared by incubating the strain in test tubes, each containing 5.0 ml of PY liquid medium for 71 hours. Then, 0.4 ml of the seed culture was inoculated with a 2-ml Komagome pipette into test tubes, each containing 8.0 ml of PY liquid medium supplemented with 0.10% DL-glutamine, 0.10% DL-histidine, 0.10% DL-isoleucine, 0.10% DL-phenylalanine, 0.10% proline, 0.10% DL-threonine, 0.10% DL-tryptophan, or 0.10% DL-valine as inducers, and cultivated for 74 hours with shaking (experiment 2).

Third, a seed culture was prepared by incubating the strain in test tubes, each containing 5.0 ml of PY liquid medium for 51 hours with shaking. The seed culture (0.4 ml) was then inoculated with a 2-ml Komagome pipette into test tubes, each containing 8.0 ml of 231 liquid medium (1.0% maltose; 0.2% N.Z.Amine, Type A; 0.1% yeast extract; 0.1% meat extract; pH 7.3) supplemented with 0.05% D-phenylalanine, 0.05% D-tryptophan, 0.05% D-valine, 0.05% L-phenylalanine, 0.05% L-tryptophan, or 0.05% L-valine as inducers, and cultivated for 48 hours with shaking (experiment 3).

From the culture broth obtained in experiments 1, 2, and 3, the cells were collected by centrifugation at 8000 rpm (7000×g) for 20 min with a refrigerated centrifuge (Hitachi Koki Co., Ltd.). The collected cells were washed with 50 mM Tris-HCl buffer (pH 7.5), collected again by centrifugation using the same centrifuge, then stored at −20° C.

The stored cells were suspended in 20 ml of 50 mM Tris-HCl buffer (pH 7.5) and were disrupted by sonication at 200 W for 15 min. The lysate was centrifuged at 15,000 rpm for 30 min with the above centrifuge, and the supernatant was obtained as a crude enzyme solution.

The enzymatic reaction was performed in 1.0 ml of a reaction system containing 20 mM N-acetyl-D-methionine, 50 mM Tris-HCl buffer (pH 7.5), 1 mM $CoCl_2$, and 100 µl of the enzyme solution at 30° C. for 20 min (experiment 1), 10 min (experiment 2), and 5 min (experiment 3). The reaction was stopped by adding a TCA solution. Tables 1, 2, and 3 show the productivity of the aminoacylase obtained in experiments 1, 2, and 3.

TABLE 1

| Inducer | Concentration of protein (mg/ml of broth) | Activity (U/ml of broth) | Specific activity (U/mg) |
|---|---|---|---|
| DL-Leucine | 3.25 | 0.315 | 0.0967 |
| N-Ac-DL-Leucine | 2.90 | 0.158 | 0.0545 |
| DL-Methionine | 3.72 | 0.177 | 0.0475 |
| N-Ac-DL-Methionine | 3.84 | 0.0713 | 0.0186 |
| DL-Valine | 3.22 | 0.429 | 0.133 |
| N-Ac-DL-Valine | 3.34 | 0.114 | 0.0341 |

TABLE 2

| Inducer | Concentration of protein (mg/ml of broth) | Activity (U/ml of broth) | Specific activity (U/mg) |
|---|---|---|---|
| DL-Glu | 3.18 | 0.0176 | 0.00553 |
| DL-His | 2.25 | 0.0144 | 0.00640 |
| DL-Ile | 2.68 | 0.214 | 0.0799 |
| DL-Phe | 2.71 | 0.190 | 0.0701 |
| DL-Pro | 3.03 | 0.00867 | 0.00286 |
| DL-Thr | 2.78 | 0.0163 | 0.00587 |
| DL-Trp | 2.61 | 0.312 | 0.119 |
| DL-Val | 2.59 | 0.239 | 0.0920 |

TABLE 3

| Inducer | Concentration of protein (mg/ml of broth) | Activity (U/ml of broth) | Specific activity (U/mg) |
|---|---|---|---|
| None | 1.62 | 0.00940 | 0.00580 |
| D-Phe | 1.58 | 0.479 | 0.303 |
| D-Trp | 1.70 | 0.913 | 0.537 |
| D-Val | 1.63 | 1.27 | 0.780 |
| L-Phe | 1.52 | 0.00973 | 0.00640 |
| L-Trp | 1.81 | 0.0243 | 0.0134 |
| L-Val | 1.65 | 0.0265 | 0.0161 |

These results clearly demonstrate that *Sebekia benihana* IFO14309 cannot induce aminoacylase without inducers, and thus this enzyme is an inducible enzyme (Table 3). D-aminoacylase was not markedly induced when DL-amino acids were used as inducers (Tables 1 and 2). In contrast, this enzyme was induced well when D-valine, D-tryptophan, or D-phenylalanine were used as inducers (Table 3).

2. Purification of D-aminoacylase (1) Preparation of Crude Enzyme Solution

*Sebekia benihana* IFO14309 was cultured in a 5-liter Erlenmeyer flask with 1 liter of 231 liquid medium containing 0.8% D-valine at 30° C. and at 160 rpm for 48 hours. After culturing, the cells were harvested by centrifugation then washed with 50 mM Tris-HCl buffer (pH 7.5). The wet cells were again collected by centrifugation and suspended in 75.0 ml of 50 mM Tris-HCl buffer (pH 7.5). The suspension was sonicated for 15 min at 190 W, then centrifuged (39,000×g for 30 min) to obtain the supernatant as a crude enzyme solution.

(2) Butyl-Toyopearl 650C Column Chromatography

Figure 1:
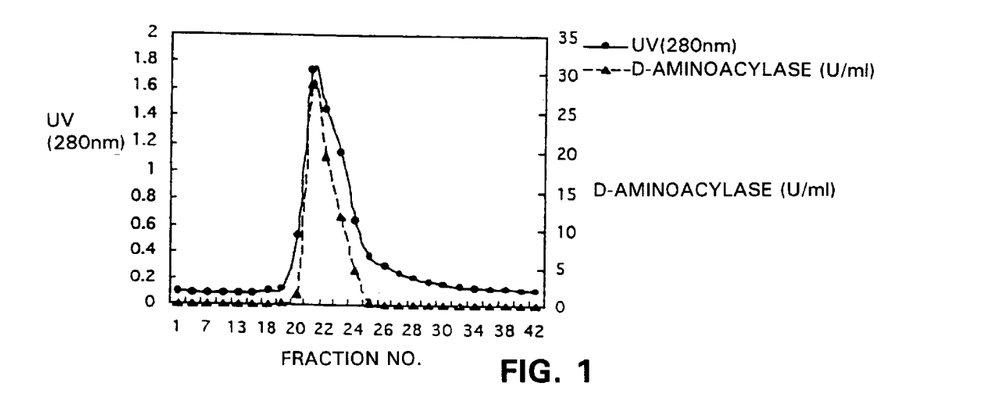
FIG. 1 shows the elution pattern of the D-aminoacylase of the present invention developed by Butyl-Toyopearl 650C column chromatography.

An 80.0 ml portion of the thus-obtained crude enzyme solution was applied to 300 ml of Butyl-Toyopearl 650C Gel equilibrated with 50 mM Tris-HCl buffer (pH 7.5) containing 1.89 M NaCl. The gel was washed with 1200 ml of 50 mM Tris-HCl buffer (pH 7.5) and eluted with 500 ml of 50 mM Tris-HCl buffer (pH 7.5) (FIG. 1). The active fractions (26.0 ml) detected by TLC were pooled in a dialysis tube (Dialysis Membrane 8, Wako Pure Chemical Industries, Ltd.) and dialyzed against a sufficient volume of 50 mM Tris-HCl buffer (pH 7.5).

(3) DEAE-Toyopearl 650M Column Chromatography

Figure 2:
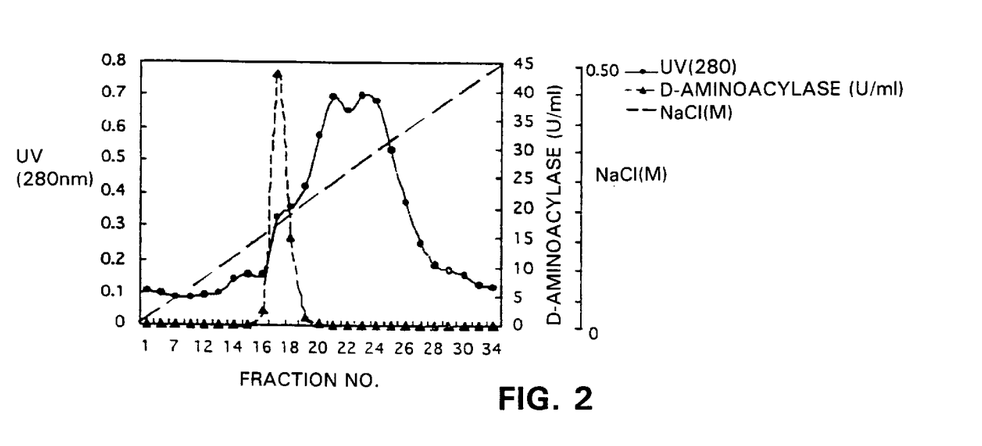
FIG. 2 shows the elution pattern of the D-aminoacylase of the present invention developed by DEAE-Toyopearl column chromatography.

A 28.0 ml portion of the dialysate as obtained above was applied to a DEAE-Toyopearl 650M column equilibrated with 50 mM Tris-HCl buffer (pH 7.5). The column was washed with 120 ml of the same buffer and eluted with a 300 ml linear gradient of NaCl from 0 to 0.50 M in 50 mM Tris-HCl buffer (pH 7.5) (FIG. 2). The active fractions (5.5 ml) detected by TLC were pooled in a dialysis tube (Dialysis Membrane 8, Wako Pure Chemical Industries, Ltd.) and dialyzed against a sufficient volume of 50 mM Tris-HCl buffer (pH 7.5).

(4) Superose 12HR10/30(FPLC)

Figure 3:
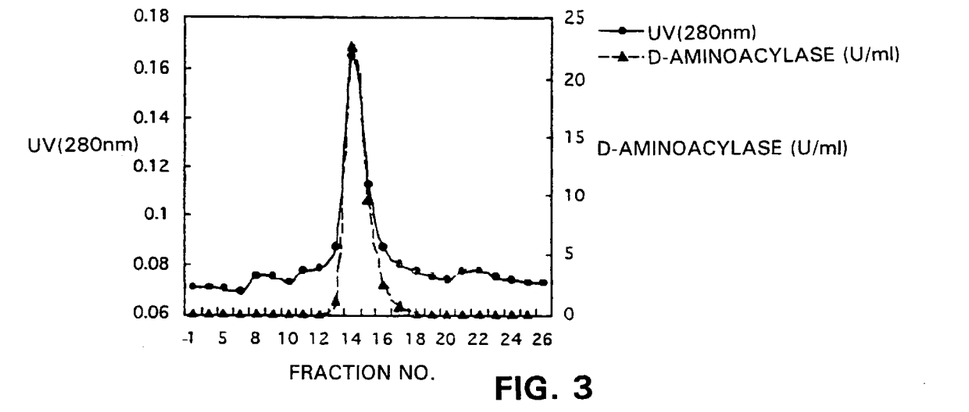
FIG. 3 shows the elution pattern of the D-aminoacylase of the present invention developed by gel filtration with Superose 12HR10/30.

The active fractions (5.5 ml) obtained by DEAE-Toyopearl 650M column chromatography were concentrated by centrifugation to 1.4 ml using an ultrafiltration membrane (ADVANTEC; molecular weight cutoff, 10,000). A 300 μl portion of the concentrate was applied to a Superose 12HR10/30 equilibrated with 50 mM Tris-HCl buffer (pH 7.5) containing 0.15 M NaCl. Elution was performed with 50 mM Tris-HCl buffer (pH 7.5) at a flow rate of 0.50 ml/min (FIG. 3).

The results obtained in each purification step are shown in Table 4.

TABLE 4

| Purification step | Volume (ml) | Total protein (mg) | Total Activity (U) | Specific activity (U/mg) | Recovery (%) | Degree of purification (fold) |
|---|---|---|---|---|---|---|
| Crude enzyme | 80 | 691 | 1544 | 2.2 | 100 | 1.0 |
| Butyl-Toyopearl (after dialysis) | 28 | 48 | 375 | 7.8 | 24 | 3.5 |
| DEAE-Toyopearl (after dialysis) | 5.5 | 1.8 | 237 | 121 | 15 | 55 |
| Superose 12 | 2.4 | 0.47 | 60 | 128 | 3.9 | 58 |

Figure 4:
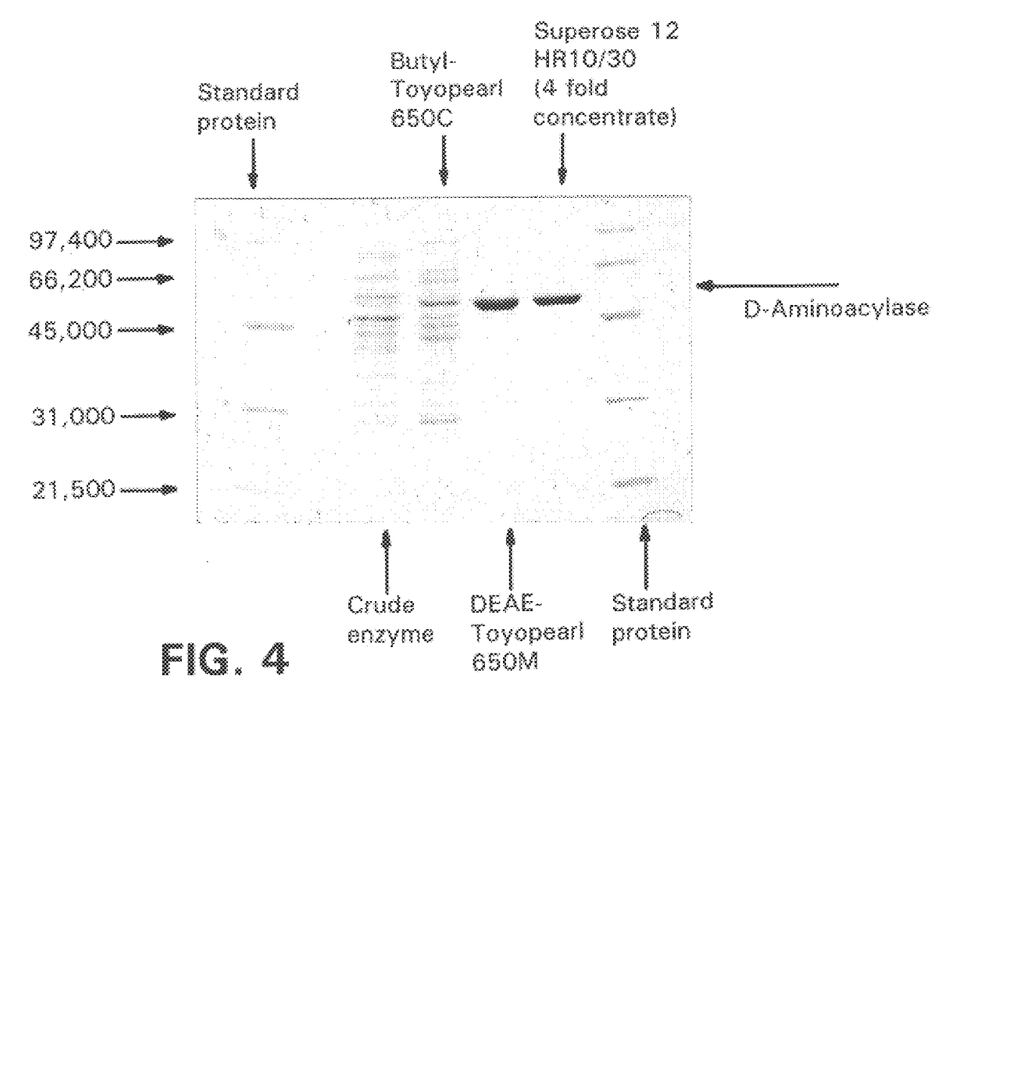
FIG. 4 shows the SDS-polyacrylamide gel electrophoresis (SDS-PAGE) patterns of the D-aminoacylase of the present invention obtained from each purification step.

The SDS-PAGE for detecting the enzyme of the present invention in each purification step was performed according to the method of Laemmli (Laemmli, U.K.: Nature, 277, pp680). Specifically, SDS-PAGE was conducted at a constant current of 30 mA with a Mini-PROTEAN II Electrophoresis Apparatus (Bio-Rad Lab.) using 4% polyacrylamide gel [0.125M Tris-HCl buffer (pH6.8), 0.1% SDS] as a stacking gel and 12.5% polyacrylamide gel [0.375M Tris-HCl buffer (pH8.8), 0.1% SDS] as a separation gel. The enzyme was mixed with the same volume of a pretreating solution [0.0625 M Tris-HCl buffer (pH6.8), 2% SDS, 2% glycerol, and 1% 2-mercaptoethanol], put in a boiling water bath for about 5 min, then cooled to room temperature. Twenty microliters of 0.5% Bromophenol Blue was added to the mixture. About 20 μl of the resulting mixture was subjected to SDS-PAGE after each of the above purification steps ((1) to (4)). As a result, the band corresponding to the desired aminoacylase was observed (FIG. 4).

The activity of the enzyme obtained in each purification step was assayed as follows. A 0.050 ml aliquot of the enzyme solution was added to 0.950 ml of 50 mM Tris-HCl buffer (pH 7.5) containing 20 mM N-acetyl-D-amino acid and incubated at 30° C. for 5 min. The reaction was then stopped by placing the reaction mixture in a boiling water bath at 95° C. for 3 min.

The active fractions were detected by TLC as follows. A 1 μl aliquot of the reaction mixture as obtained above and 1 mM L-methionine as a standard were spotted on a TLC plate (Silica gel 60F$_{254}$, Merck) and developed with n-butanol:acetic acid:water (3:1:1). The plate was sprayed with a ninhydrin reagent (0.20 g ninhydrin, 95 ml n-butanol, and 5 ml 2N acetic acid) then heated to 170° C. to visualize the active fractions.

Amino acids were determined by HPLC using 1 nertsi-1ODS10 column (mobile phase, acetonitrile: 50 mM acetate buffer (30:70 (v/v)); 2.0 mM DL-methionine was used as a standard. The protein content was determined by the Lowry method using bovine serum albumin (BSA) as a standard (Schmidt, G. & Thornhauser, S. J.: J. Biol. Chem. 161, pp83 (1945)).

EXAMPLE 2

Properties of Aminoacylase Derived From *Sebekia benihama* IFO14309

1. Substrate Specificity

The substrate specificity of the aminoacylase was examined using N-acetyl-D-methionine, N-acetyl-D-alanine, N-acetyl-D-aspartic acid, N-acetyl-D-leucine, N-acetyl-D-phenylalanine, N-acetyl-D-tryptophan, N-acetyl-D-valine, N-acetyl-L-leucine, N-acetyl-L-methionine, and N-acetyl-L-valine as substrates. The enzyme activity was assayed as follows. A 0.050-ml aliquot of an enzyme solution was added to 0.950 ml of 20 mM N-acetyl-D(or L)-amino acid in 50 mM Tris-HCl buffer (pH 7.5) and incubated at 30° C. for 5 min. The reaction was then stopped by adding 0.50 ml of a TCA solution to the reaction mixture. The relative activity is shown in Table 5, taking the activity for N-acetyl-L-methionine as 100%.

TABLE 5

| Substrate | Relative activity (%) |
|---|---|
| N-Ac-D-Met | 100 |
| N-Ac-D-Ala | 1.1 |
| N-Ac-D-Asn | 1.4 |
| N-Ac-D-Leu | 255 |
| N-Ac-D-Phe | 100 |
| N-Ac-D-Trp | 64 |
| N-Ac-D-Val | 33 |
| N-Ac-L-Leu | 0* |
| N-Ac-L-Met | 0** |
| N-Ac-L-Val | 0** |

*Less than 1% impurities (D-form)
**Less than 2% impurities (D-form)

2. Determining Molecular Weight

The molecular weight of the enzyme was measured by (1) SDS-PAGE, (2) gel filtration (FPLC), and (3) gel filtration (HPLC).

(1) SDS-PAGE

Figure 5:
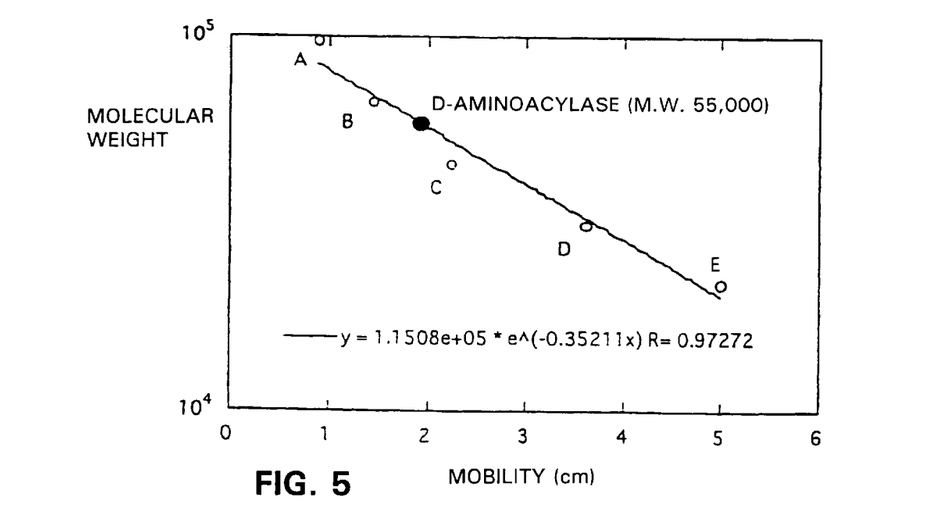
FIG. 5 shows the results of determining the molecular weight of the D-aminoacylase of the present invention by SDS-PAGE. In the figure, A represents phosphorylase b (97 k); B, bovine serum albumin (66 k); C, ovalbumin (45 k); D, carbonic anhydrase (30 k); and E, trypsin inhibitor (21 k).

SDS-PAGE was performed according to the method described above at a constant current of 30 mA using an electrophoresis apparatus (Thermostat Minislab Gel Electrophoresis Apparatus NA-1012, Nihhon Eido). Phosphorylase (97 k), bovine serum albumin (66 k), ovalbumin (45 k), carbonic anhydrase (30 k), and trypsin inhibitor (21 k) were used as molecular weight markers (Bio-Rad Lab.). The molecular weight of the enzyme was estimated to be approximately 55,000 daltons (FIG. 5).

(2) Gel Filtration (FPLC)

Figure 6:
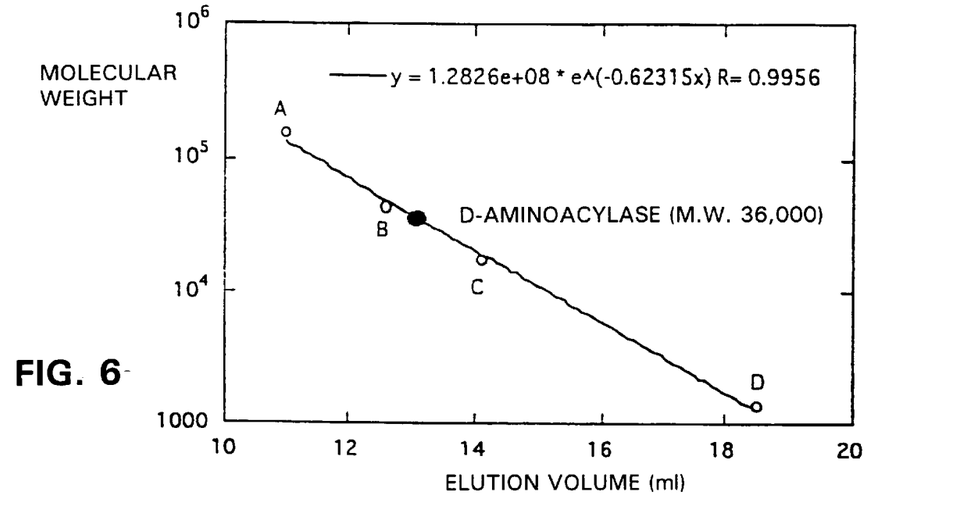
FIG. 6 shows the results of determining the molecular weight of the D-aminoacylase of the present invention by gel filtration (FPLC). In the figure, A represents gamma-globulin (158 k); B, ovalbumin (45 k); C, mypglobin (17 k); and D, vitamine B-12 (1.35 k).

FPLC was performed using the above-described Superose 12HR10/30 (Pharmacia) column at a flow rate of 0.50 ml/min. Gamma globulin (158 k), ovalbumin (45 k), myoglobulin (17 k), and vitamin B-12 (1.35 k) (Bio-Rad Lab.) were used as molecular weight markers. As a result, the molecular weight of the enzyme was estimated to be approximately 36,000 daltons (FIG. 6).

(3) Gel Filtration (HPLC)

Figure 7:
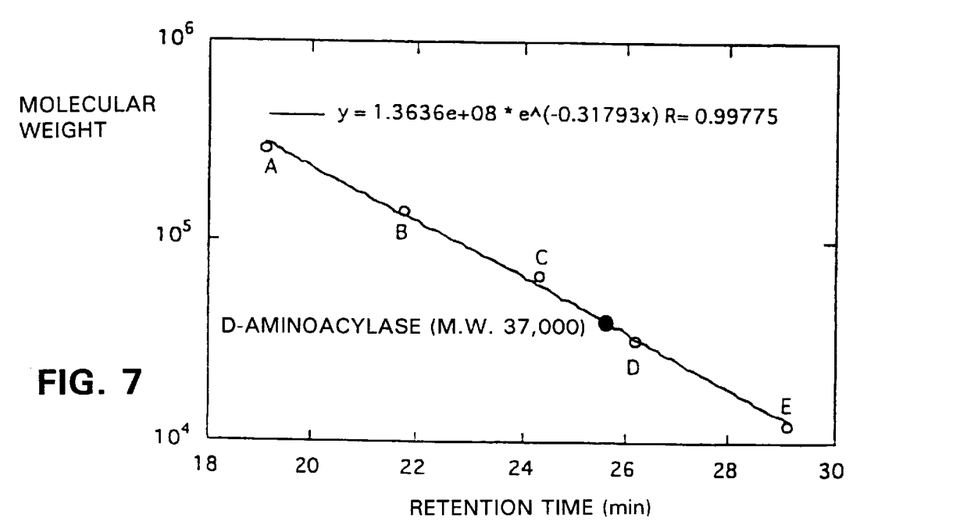
FIG. 7 shows the results of determining the molecular weight of the D-aminoacylase of the present invention by gel filtration (HPLC). In the figure, A represents glutamate dehydrogenase (290 k); B, lactate dehydrogenase (140 k); C, enolase (67 k); D, adenylate cyclase (32 k); and E, cytochrome c (12.4 k).

An HPLC system (Shimadzu Co.) with a G3000SWXL (I.D.7.8×300 mm) column was used. Glutamate dehydrogenase (290 k), lactate dehysrogenase (140 k), enolase (67 k), adenylcyclase (32 k), and cytochrome C (12.4 k) were used as molecular weight markers (oriental Yeast Co., Ltd.). The flow rate was 0.35 ml/min. As a result, the molecular weight of the enzyme was estimated to be approximately 37,000 daltons (FIG. 7).

3. Properties of the Enzyme (1) Thermostability

Figure 8:
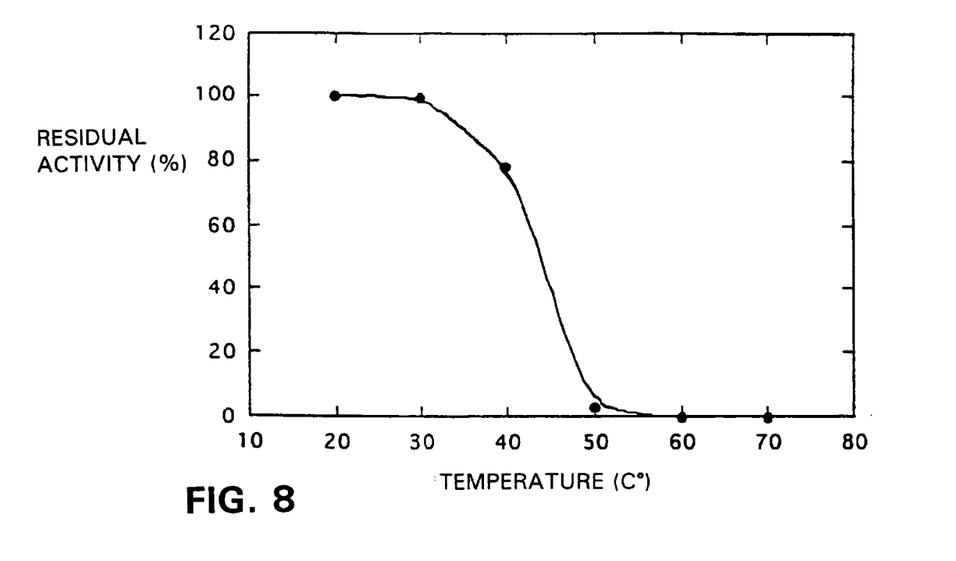
FIG. 8 shows the thermostability of the D-aminoacylase of the present invention.

The enzyme solutions were incubated at 20° C., 30° C., 50° C., and 60° C. for 30 min then immediately cooled with ice. The resulting enzyme solutions were subjected to the enzyme reaction at 30° C. for 5 min in 1.0 ml of 50 mM Tris-HCl buffer (pH 7.5) containing 20 mM N-acetyl-D-methionine. The thermostability of the enzyme is shown in Table 6 and FIG. 8. This enzyme is stable up to 40° C., but deactivated at 50° C. or above.

TABLE 6

|  | Concentration of D-Met (mM) | Relative activity (100%) |
| --- | --- | --- |
| 20° C. | 1.5 | 100 |
| 30° C. | 1.5 | 100 |
| 40° C. | 1.1 | 73 |
| 50° C. | 0.045 | 3.1 |
| 60° C. | 0 | 0 |
| 70° C. | 0 | 0 |

(2) Optimum Temperature

Figure 9:
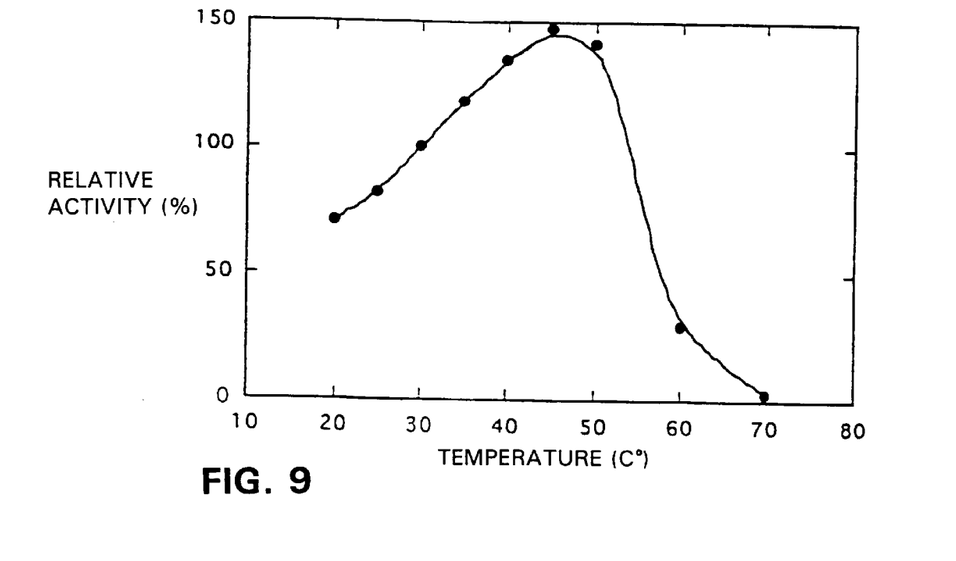
FIG. 9 shows the optimum temperature of the D-aminoacylase of the present invention.

The enzymatic reaction was performed in the same manner as in (1) with the temperature ranging from 20° C. to 70° C. As shown in Table 7 and FIG. 9, the optimum temperature was estimated to be approximately 45° C.

TABLE 7

|  | Concentration of D-Met (mM) | Relative activity (100%) |
| --- | --- | --- |
| 20° C. | 1.1 | 73 |
| 25° C. | 1.2 | 80 |
| 30° C. | 1.5 | 100 |
| 35° C. | 1.8 | 120 |
| 40° C. | 2.0 | 133 |
| 45° C. | 2.2 | 147 |
| 50° C. | 2.1 | 140 |
| 60° C. | 0.46 | 31 |
| 70° C. | 0.052 | 3.5 |

(3) Optimum pH

Figure 10:
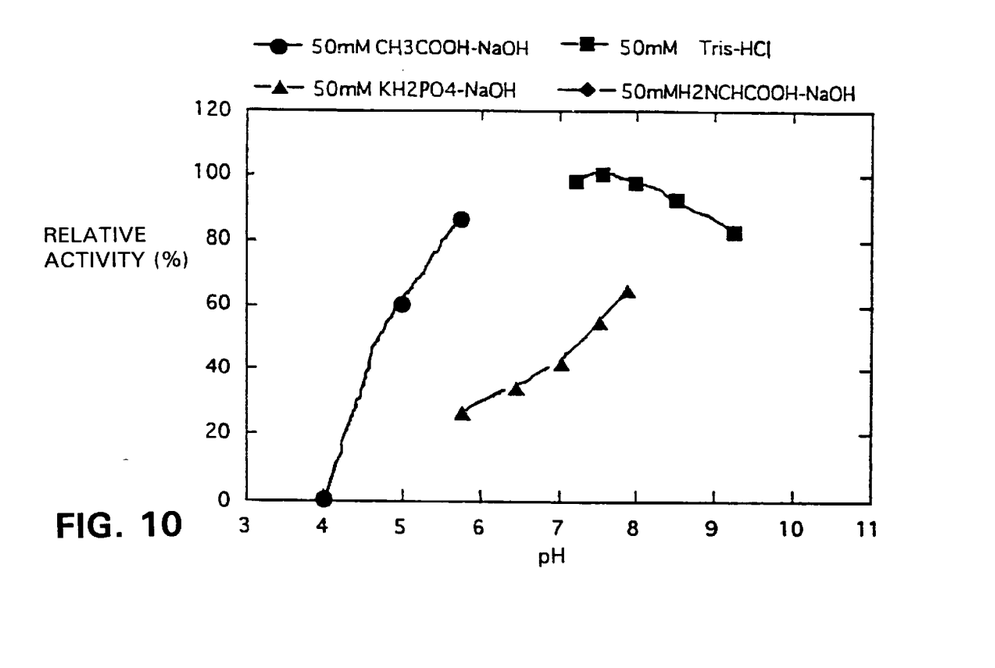
FIG. 10 shows the optimum pH of the D-aminoacylase of the present invention. In the figure, circles represent $CH_3COOH$—NaOH buffer; triangles, $KH_2PO_4$—NaOH buffer; squares, Tris-HCl buffer; diamonds, glycine-NaOH buffer.

The enzymatic reaction was performed in the same manner as in (1) at 30° C. for 5 min except the pH values were varied from 4.0 to 10.5. The following buffer systems were used: 50 mM $CH_3COOH$—NaOH buffer (pH4.0, 5.0, and 5.8), 50 mM $KH_2PO_4$—NaOH buffer (pH5.8, 6.5, 7.0, 7.5, and 8.0), 50 mM Tris-HCl buffer (pH7.2, 7.5, 8.0, 8.5, and 9.2), and 50 mM glycine-NaOH buffer (pH8.5, 9.5, and 10.5). As shown in Table 8 and FIG. 10, the optimum pH of the enzyme was estimated to be about pH7.5 to 8.5. No activity was detected under acidic conditions (pH4 or below).

TABLE 8

|  | Concentration Of D-Met (mM) | Relative activity (%) |
| --- | --- | --- |
| 50 mM $CH_3COOH$—NaOH pH 4.0 | 0 | 0 |
| 50 mM $CH_3COOH$—NaOH pH 5.0 | 0.99 | 62 |
| 50 mM $CH_3COOH$—NaOH pH 5.8 | 1.4 | 88 |
| 50 mM $KH_2PO_4$—NaOH pH 5.8 | 0.44 | 28 |
| 50 mM $KH_2PO_4$—NaOH pH 6.5 | 0.58 | 36 |
| 50 mM $KH_2PO_4$—NaOH pH 7.0 | 0.70 | 44 |
| 50 mM $KH_2PO_4$—NaOH pH 7.5 | 0.90 | 56 |
| 50 mM $KH_2PO_4$—NaOH pH 8.0 | 1.1 | 69 |
| 50 mM Tris-HCl pH 7.2 | 1.6 | 100 |
| 50 mM Tris-HCl pH 7.5 | 1.6 | 100 |
| 50 mM Tris-HCl pH 8.0 | 1.6 | 100 |
| 50 mM Tris-HCl pH 8.5 | 1.5 | 94 |
| 50 mM Tris-HCl pH 9.2 | 1.4 | 88 |

(4) pH Stability

Figure 11:
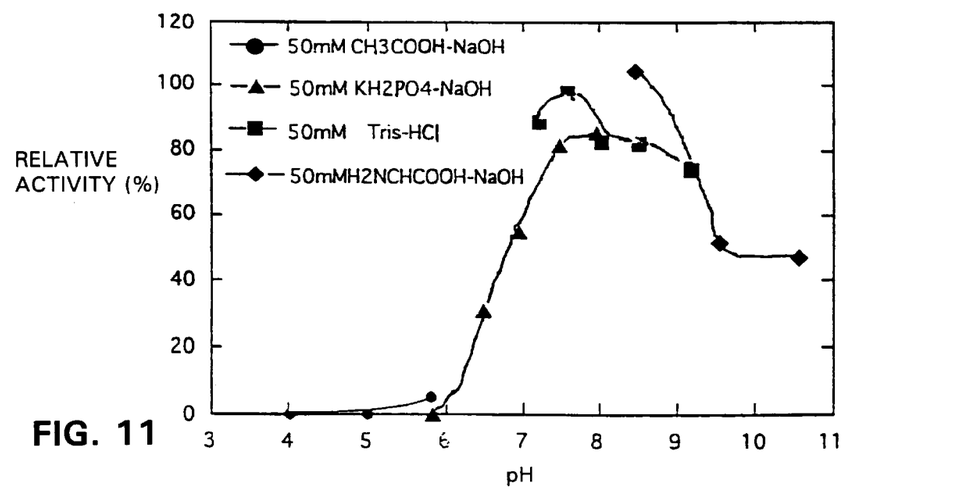
FIG. 11 shows the pH stability of the D-aminoacylase of the present invention. In the figure, circles represent $CH_3COOH$—NaOH buffer; triangles, $KH_2PO_4$—NaOH buffer; squares, Tris-HCl buffer; diamonds, glycine-NaOH buffer.

After the enzyme was maintained at 4° C. for 20 hours at various pHs, the enzymatic reaction was performed in the same manner as in (1). The following buffer systems were used: 50 mM $CH_3COOH$—NaOH buffer (pH4.0, 5.0, and 5.8), 50 mM $KH_2PO_4$—NaOH buffer ( pH5.8, 6.5, 7.0, 7.5, and 8.0), 50 mM Tris-HCl buffer (pH7.2, 7.5, 8.0, 8.5, and 9.2), and 50 mM glycine-NaOH buffer(pH8.5, 9.5, and 10.5). The pH stability of the enzyme is shown in Table 9 and FIG. 11.

TABLE 9

|  | Concentration of D-Met (mM) | Relative activity (%) |
| --- | --- | --- |
| 50 mM $CH_3COOH$—NaOH pH 4.0 | 0 | 0 |
| 50 mM $CH_3COOH$—NaOH pH 5.0 | 0 | 0 |
| 50 mM $CH_3COOH$—NaOH pH 5.8 | 0.057 | 4.9 |
| 50 mM $KH_2PO_4$—NaOH pH 5.8 | 0 | 0 |
| 50 mM $KH_2PO_4$—NaOH pH 6.5 | 0.39 | 34 |
| 50 mM $KH_2PO_4$—NaOH pH 7.0 | 0.68 | 59 |
| 50 mM $KH_2PO_4$—NaOH pH 7.5 | 0.94 | 82 |
| 50 mM $KH_2PO_4$—NaOH pH 8.0 | 0.98 | 85 |
| 50 mM Tris-HCl pH 7.2 | 1.0 | 87 |
| 50 mM Tris-HCl pH 7.5 | 1.2 | 100 |
| 50 mM Tris-HCl pH 8.0 | 0.96 | 83 |
| 50 mM Tris-HCl pH 8.5 | 0.97 | 84 |
| 50 mM Tris-HCl pH 9.2 | 0.88 | 76 |
| 50 mM Glycine-NaOH pH 8.5 | 1.2 | 104 |
| 50 mM Glycine-NaOH pH 9.5 | 0.60 | 52 |
| 50 mM Glycine-NaOH pH 10.5 | 0.56 | 48 |

(5) Influences of Various Metal Salts and Inhibitors

The enzymatic reaction was performed in the same manner as in (1) except that the metal salts and enzyme inhibitors listed in Tables 10 and 11 (1 mM or 10 mM) were added to the reaction mixture. Tables 10 and 11 show influences of the metal salts and inhibitors on the activity of the enzyme.

TABLE 10

| Metal Salt | 1 mM | | 10 mM | |
| --- | --- | --- | --- | --- |
| | D-Met (mM) | Residual activity (%) | D-Met (mM) | Residual activity (%) |
| None | 1.2 | 100 | 1.2 | 100 |
| BaCl$_2$ | 1.2 | 100 | 1.1 | 92 |
| CaCl$_2$ | 1.3 | 108 | 1.1 | 92 |
| CoCl$_2$ | 0.65 | 54 | 0.11 | 9.2 |
| CuCl$_2$ | 0.13 | 11 | 0 | 0 |
| FeCl$_2$ | 0.24 | 20 | 0.035 | 2.9 |
| HgCl$_2$ | 0.38 | 32 | 0 | 0 |
| KCl | 1.2 | 100 | 1.1 | 92 |
| MgCl$_2$ | 1.3 | 108 | 1.2 | 100 |
| MnCl$_2$ | 1.3 | 108 | 0.73 | 61 |
| NaCl | 1.3 | 108 | 1.1 | 92 |
| NiCl$_2$ | 0.53 | 44 | 0.035 | 2.9 |
| ZnCl$_2$ | 0.50 | 42 | 0 | 0 |
| EDTA · 2Na | 1.2 | 100 | 1.3 | 108 |

TABLE 11

| Inhibitor | 1 mM | | 10 mM | |
| --- | --- | --- | --- | --- |
| | D-Met (mM) | Residual activity (%) | D-Met (mM) | Residual activity (%) |
| None | 1.6 | 100 | 1.6 | 100 |
| 2,2'-Bipyridyl | 1.6 | 100 | 1.4 | 88 |
| N-ethyl-maleimide | 1.7 | 106 | 1.1 | 69 |
| ICH$_2$COOH | 1.3 | 81 | 0.070 | 4.4 |
| PCMB* | 1.8 | 112 | 1.6 | 100 |
| DTT | 0.13 | 8.1 | 0.055 | 3.4 |
| EDTA | 1.6 | 100 | 1.6 | 100 |
| NaF | 1.6 | 100 | 1.4 | 88 |

*PCMB was used at 0.01 mM and 0.1 mM.

The enzyme does not require any metal ion to promote its activity. The enzyme was inhibited by $Cu^{2+}$, $Fe^{2+}$, $Ni^{2+}$, $Zn^{2+}$, $Co^{2+}$, and $Hg^{2+}$. It was also inhibited by p-chloromercuribenzoic acid (PCMB) that is an SH reagent, iodoacetic acid, and EDTA that is a chelating agent.

What is claimed is:

1. A D-aminoacylase having the following physicochemical properties:
   (a) Action: acting on N-acetyl-D-amino acid to produce D-amino acid;
   (b) Molecular weight: about 55,000 daltons determined by SDS-polyacrylamide gel electrophoresis and about 36,000 to about 37,000 daltons determined by gel filtration;
   (c) Substrate specificity: acting on N-acetyl-D-methionine, N-acetyl-D-valine, N-acetyl-D-tryptophan, N-acetyl-D-asparagine, N-acetyl-D-phenylalanine, N-acetyl-D-alanine and N-acetyl-D-leucine, but not on N-acetyl-L-methionine, N-acetyl-L-leucine, and N-acetyl-L-valine;
   (d) Thermostability: stable at 40° C. and inactivated at 50° C. or above when heated at pH 7.5 for 30 minutes;
   (e) Optimum temperature: optimally active at about 45° C. when reacted at pH 7.5;
   (f) Optimum pH: optimally active at a pH of about 7.5 to about 8.5 when reacted at 30° C. for 30 minutes; and
   (g) Effects of metal ions: requiring no metal ion, but inhibited by 1 mM of $Cu^{2+}$, $Hg^{2+}$, $Ni^{2+}$, $Fe^{2+}$, $Co^{2+}$, and $Zn^{2+}$.

2. The D-aminoacylase of claim 1, wherein said enzyme is derived from a microorganism belonging to the genus Sebekia.

3. The D-aminoacylase of claim 2, wherein said microorganism is *Sebekia benihana*.

4. A method of producing the D-aminoacylase of claim 1, which comprises culturing a microorganism belonging to the genus Sebekia and recovering from the culture an enzyme having the following properties:
   (a) Action: acting on N-acetyl-D-amino acid to produce D-amino acid;
   (b) Molecular weight: about 55,000 daltons determined by SDS-polyacrylamide gel electrophoresis and about 36,000 to about 37,000 daltons determined by gel filtration;
   (c) Substrate specificity: acting on N-acetyl-D-methionine, N-acetyl-D-valine, N-acetyl-D-tryptophan, N-acetyl-D-asparagine, N-acetyl-D-phenylalanine, N-acetyl-D-alanine and N-acetyl-D-leucine, but not on N-acetyl-L-methionine, N-acetyl-L-leucine, and N-acetyl-L-valine;
   (d) Thermostability: stable at 40° C. and inactivated at 50° C. or above when heated at pH 7.5 for 30 minutes;
   (e) Optimum temperature: optimally active at about 45° C. when reacted at pH 7.5;
   (f) Optimum pH: optimally active at a pH of about 7.5 to about 8.5 when reacted at 30° C. for 30 minutes; and
   (g) Effects of metal ions: requiring no metal ion, but inhibited by 1 mM of $Cu^{2+}$, $Hg^{2+}$, $Ni^{2+}$, $Fe^{2+}$, $Co^{2+}$, and $Zn^{2+}$.

5. The method of claim 4, wherein said microorganism is *Sebekia benihana*.

6. A method of producing D-amino acid which comprises reacting N-acetyl-DL-amino acid with the D-aminoacylase of claim 1 and recovering D-amino acid from the reaction mixture.

7. The method of claim 6, wherein said N-acetyl-DL-amino acid is selected from the group consisting of N-acethyl-DL-methionine, N-acethyl-DL-valine, N-acethyl-DL-tryptophan, N-acethyl-DL-asparagine, N-acethyl-DL-phenylalanine, N-acethyl-DL-alanine, and N-acethyl-DL-leucine.

* * * * *